United States Patent [19]

Cope

[11] Patent Number: 5,032,024

[45] Date of Patent: Jul. 16, 1991

[54] OPTICAL EXAMINATION APPARATUS

[75] Inventor: Mark Cope, London, England

[73] Assignee: Hamamatsu Photonics Kabushiki Kaisha, Shizuoka, Japan

[21] Appl. No.: 345,260

[22] Filed: May 1, 1989

[30] Foreign Application Priority Data

Feb. 6, 1989 [GB] United Kingdom ................. 8902562

[51] Int. Cl.[5] ...................... G01N 33/48; G01N 21/01; G02B 6/04; A61B 5/00

[52] U.S. Cl. ...................................... 356/41; 356/435; 350/96.24; 128/633

[58] Field of Search ............... 128/633, 634; 356/73.1, 356/435, 41, 419, 73; 350/96.24, 96.22, 96.20, 96.15; 358/901; 250/227

[56] References Cited

U.S. PATENT DOCUMENTS

| | | | |
|---|---|---|---|
| 3,885,879 | 5/1975 | Louder et al. | 356/419 |
| 3,992,110 | 11/1976 | Frazer et al. | 356/419 |
| 4,281,645 | 8/1981 | Jobsis | 128/633 |
| 4,908,762 | 4/1990 | Suzuki et al. | 356/434 |

FOREIGN PATENT DOCUMENTS 63-275329 11/1988 Japan .

*Primary Examiner*—Vincent P. McGraw
*Assistant Examiner*—LaCharles P. Keesee
*Attorney, Agent, or Firm*—Finnegan, Henderson, Farabow, Garrett and Dunner

[57] ABSTRACT

An optical examination apparatus for optically examining density, distribution, etc. of oxygen in an object to be examined such as organic tissue like brain tissue, of man or animal compressing a light source, an optical fibre bundle having one end on which light emitted from the light source is incident and which is divided at the other end into a first and second branch with a predetermined ratio of division, transmitted and scattered light detection means for detecting light is emitted from the first branch of the fibre bundle and transmitted through and scattered by the object to be examined, monitoring light detection means for detecting monitoring light emitted from the second branch fibre bundle, normalization means for normalizing an output of the transmitted and scattered light detected means on the basis of an output from the monitoring light detection means, representative sampling means for ensuring that the light output from the second branch fibre bundle is representative of that output by the light source. The representative sampling means may be provided by distributing the optical fibres forming the second branch fibre bundle uniformly over the one end of the optical fibre bundle or may comprise a mode scrambler interposed between the one end of the optical fibre bundle and the light source to distribute light from the light source over the whole fibre bundle.

6 Claims, 5 Drawing Sheets

OPTICAL EXAMINATION APPARATUS

BACKGROUND OF THE INVENTION

The present invention relates to an optical examination apparatus for optically examining density, distribution, etc. of oxygen in an object to be examined such as organic tissue like brain tissue, of man or animal.

U.S. Pat. No. 4,281,645 discloses one such technique, in which light emitted from a laser light source is led to brain tissue through an optical fibre bundle, and light is transmitted and scattered by the brain tissues. The laser light source emits near infrared light and may operate at a number of different wavelengths and then the measurement is made at every wavelength.

However, a laser light source, particularly a semiconductor laser, has a problem in that it is not easy to stabilize its output power and variations in the output power are different at different wavelengths, so that the reliability of the result of examination by means of the examination apparatus is lowered. To overcome this problem there has previously been proposed in Japanese Patent Application Unexamined Publication No. 275329/1988 sampling the light output by the light source and using this to normalize the output of the detector which detects the transmitted and scattered light. This arrangement is shown in FIG. 4.

As shown in FIG. 4, an apparatus to measure transmitted and scattered light $P_A$ from organic tissues 1 comprises a laser light source 2, a transmitted and scattered light detector 3, a monitoring light detector 4, and a normalizing device 5. The light emitted from the laser light source 2 is incident on an optical fibre bundle 6 at one end so that the light is partly led to the organic tissues 1 through a first branch fibre bundle 61, and is partly led to the monitoring light detector 4 through a second branch fibre bundle 62. The transmitted and scattered light $P_A$ produced from the organic tissues 1 is led to the transmitted and scattered light detector 3 through another optical fibre bundle 7. The respective outputs detected by the transmitted and scattered light detector 3 and the monitoring light detector 4 are transferred in the form of electric signals to the normalizing device 5. In the normalizing device 5, the transmitted and scattered light output $S_A$ is normalized in accordance with the monitored light output $S_M$. In the past, When a number of, for example, four, laser light sources $2_1$ to $2_4$ each having a distinct wavelength $\lambda_1$ to $\lambda_4$, respectively, are provided, a corresponding number (four) of optical fibre bundles $6_1$ to $6_4$ are provided as shown in FIG. 5. Thus, the output power of the laser light source 2 is monitored and the transmitted and scattered light output $S_A$ is normalized in accordance with the monitored output power, so that the unevenness due to variations in output in the results of measurements can be compensated for once the apparatus is calibrated for all powers and wavelengths.

Examples of the optical fibre bundle 6 which may used in the conventional apparatus are shown in FIGS. 6 and 7. FIG. 6 shows an optical fibre bundle in which two optical fibres are combined. As shown in the drawing, the laser light emitted from the laser chip 22 fixed to a laser casing 21 is transmitted through a glass window 23. The transmitted light is focused by lenses $L_1$ and $L_2$ to be incident on an optical fibre 68 provided at their focus, and then propagated toward the organic tissue 1. On the other hand, another optical fibre 69 is provided adjacent the optical fibre 68, so that laser light displaced from the focus point is incident on that optical fibre 69. Accordingly, if the light propagated through the optical fibre 69 is monitored, the normalization described above can be carried out.

FIG. 7(*a*) shows another optical fibre bundle in which a number of optical fibres are combined. As seen in the drawings, the optical fibre bundle 6 is split into a first branch fibre bundle 61 for propagating light to the organic tissues and a second branch fibre bundle 62 for propagating light to the monitored light detector 4. The ends of the plurality of optical fibres constituting the second branch fibre bundle 62 are however unevenly distributed over the end face at a portion inside a coating 63 to one side as represented by the circle shown in FIG. 7(*b*).

In the light source 2, particularly when this includes a semiconductor laser however, variations may occur not only in its output power but in its luminous pattern. That is, in such a semiconductor laser 90 as shown in FIG. 8, laser light is emitted from a stripe region 92 of an active layer 91 with a luminous pattern 93 having a substantially eliptical shape. We have discovered, as shown in FIG. 9, that when the second monitoring branch fibre bundle 62 is located to one side of the optical fibre bundle 6 the overlap between the output and the input ends of the monitoring branch fibre bundle 62 varies. That is, when the luminous pattern $93_1$ has a large oval shape as shown in FIG. 9(*a*), the monitoring output is large, but when the luminous pattern $93_3$ has a small oval shape as shown in FIG. 9(*c*), the monitoring output is small.

FIG. 10 shows the ratio between the output characteristic of the monitoring or second branch fibre bundle 62 with respect to that of the first bundle 61. In the drawing, the axis of ordinate shows the output of the first branch fibre bundle 61 for introducing light to organic tissues, and the axis of abscissa shows the output of the second branch fibre bundle 62 for monitoring. The graph illustrates how the measured data is shifted from a linear relationship where the solid line is a regression line of the measured data.

SUMMARY OF THE INVENTION

An object of the present invention is to provide an examination apparatus which can accurately examine an object in spite of variations not only in luminous output but also in luminous pattern from a laser light source.

According to this invention an optical examination apparatus comprises:

a light source;

an optical fibre bundle having one end on which light emitted from the light source is incident and which is divided at the other end into a first and second branch with a predetermined ratio of division;

a transmitted and scattered light detection means for detecting light which is emitted from the first branch fibre bundle and, in use, is transmitted through and scattered by an object to be examined;

a monitoring light detection means for detecting monitoring light emitted from the second branch fibre bundle;

normalization means for normalizing an output of the transmitted and scattered light detection means on the basis of an output from the monitoring light detection means; and, representative sampling means to ensure that the light output from the second branch fibre bundle is representative of that output by the light source.

The representative sampling means may be provided by distributing the optical fibres forming the second branch fibre bundle uniformly over the one end of the optical fibre bundle. Alternatively they may comprise a mode scrambler interposed between the one end of the optical fibre bundle and the light source to distribute light from the light source over the whole fibre bundle.

With the arrangements in accordance with the present invention, in spite of the variations in the luminous pattern of the light source as a result of changes in intensity and wavelength, the light output from the second branch fibre bundle is always representative of the light output of the light source so that the variations in its luminous output can be accurately monitored and compensated for.

Other and further objects, features and advantages of the invention will appear more fully from the following description taken in connection with the accompanying drawings.

BRIEF DESCRIPTION OF THE DRAWINGS

FIG. 1(*b*) is a cross-section taken along the line A—A shown in FIG. 1(*a*);

FIG. 2(*b*) is a cross-section taken along the line A—A shown in FIG. 2(*a*);

DETAILED DESCRIPTION OF THE PREFERRED EMBODIMENTS

Preferred embodiments of the present invention will now be described with reference to the accompanying drawings.

Figure 1A:
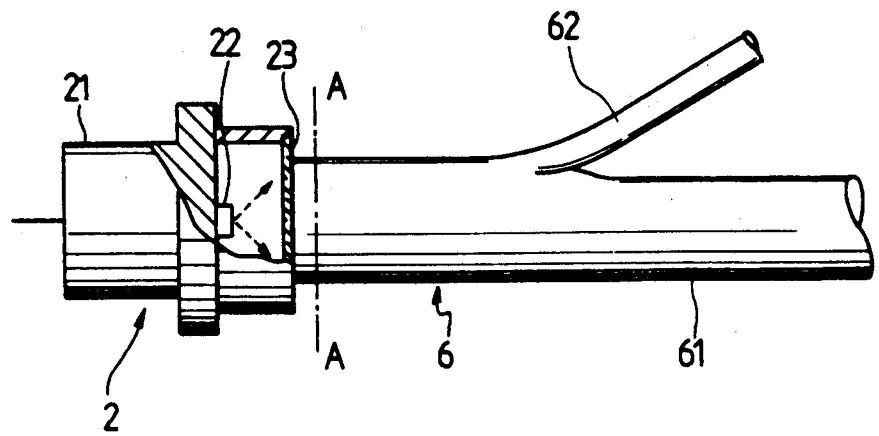
FIG. 1(*a*) is a partly sectioned side elevation of a main portion of a first example of the present invention.
Figure 1B:
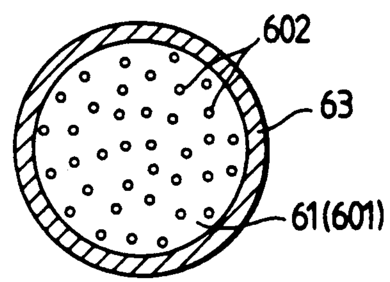
Figure 4:
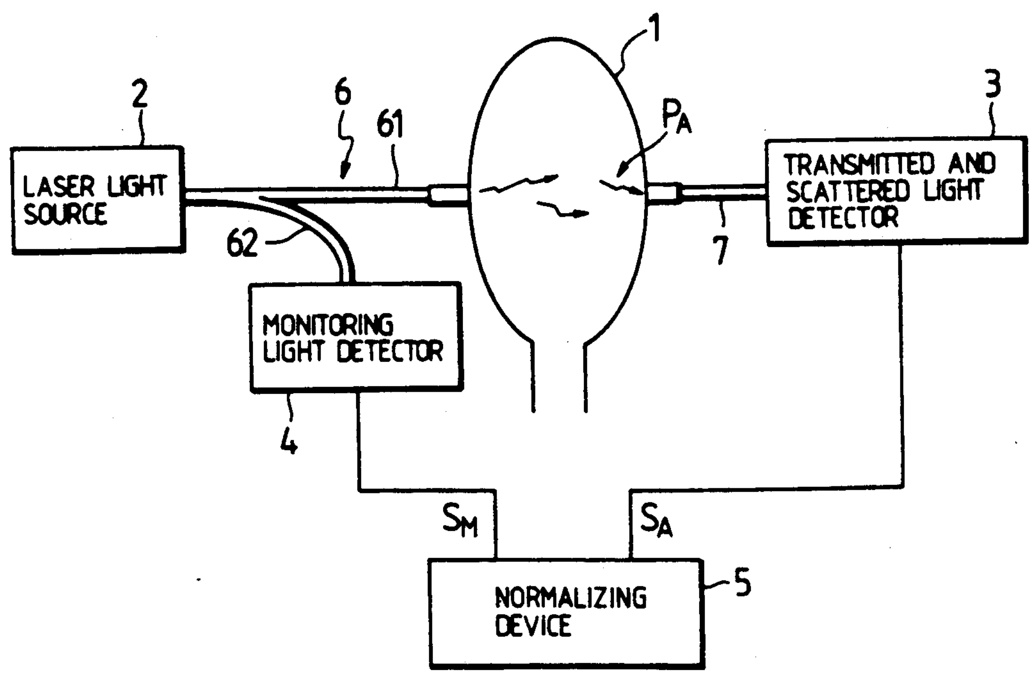
FIG. 4 is a block diagram showing the arrangement of the whole optical examination apparatus.

FIGS. 1(*a*) and 1(*b*) show a main portion of a first example of an examination apparatus in accordance with the present invention which is generally similar to that shown in FIG. 4 but in which the optical fibre bundle is replaced by that shown in FIGS. 1(*a*) and (*b*). This example is different from the conventional optical fibre bundle shown in FIG. 7 in that a plurality of optical fibres 602 constituting the second branch fibre bundle 62 for monitoring are distributed uniformly about the incident face and mixed up with the plurality of optical fibres 601 constituting the first branch fibre bundle 61 for light emission. Accordingly, even if a luminous pattern of a laser chip 22 varies with intensity or wavelength, its luminous output is accurately monitored since the second bundle 62 always carries the same proportion of the light incident on the end face.

Figure 2A:
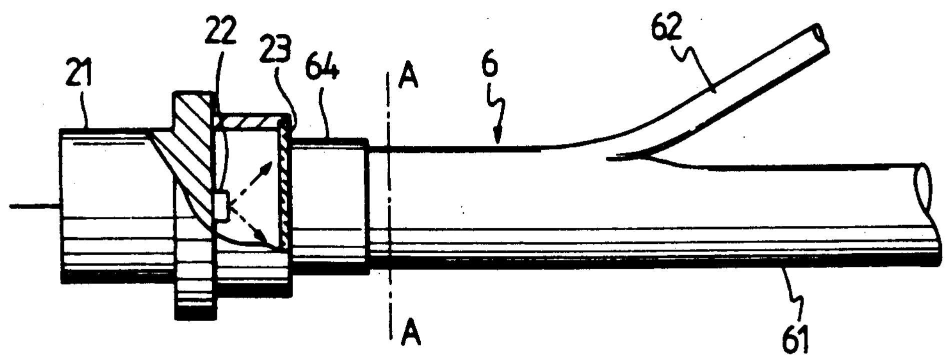
FIG. 2(*a*) is a partly sectioned side elevation of a main portion of a second example of the present invention.
Figure 2B:
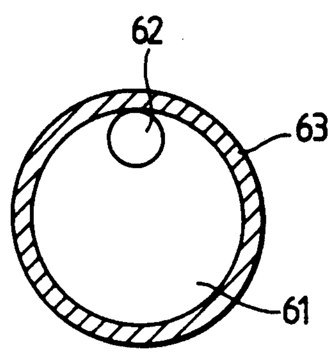
Figure 7A:
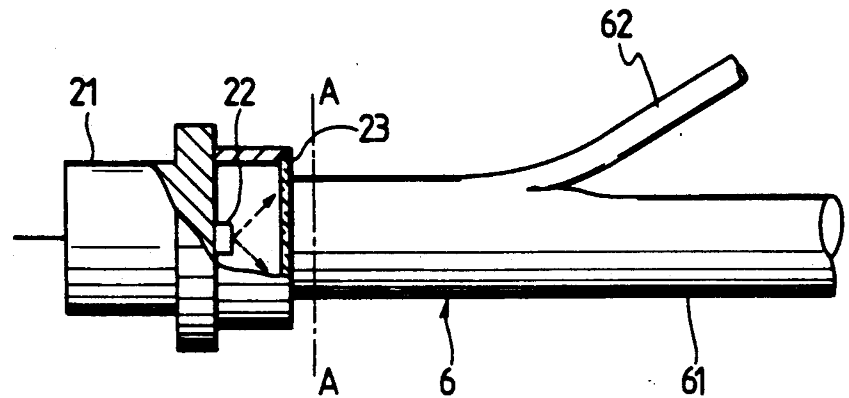
Figure 7B:
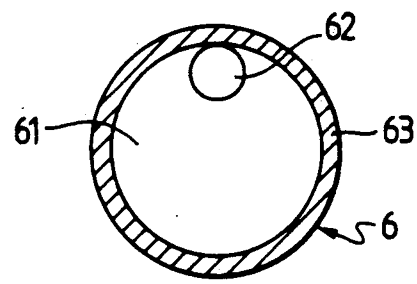
Figure 8:
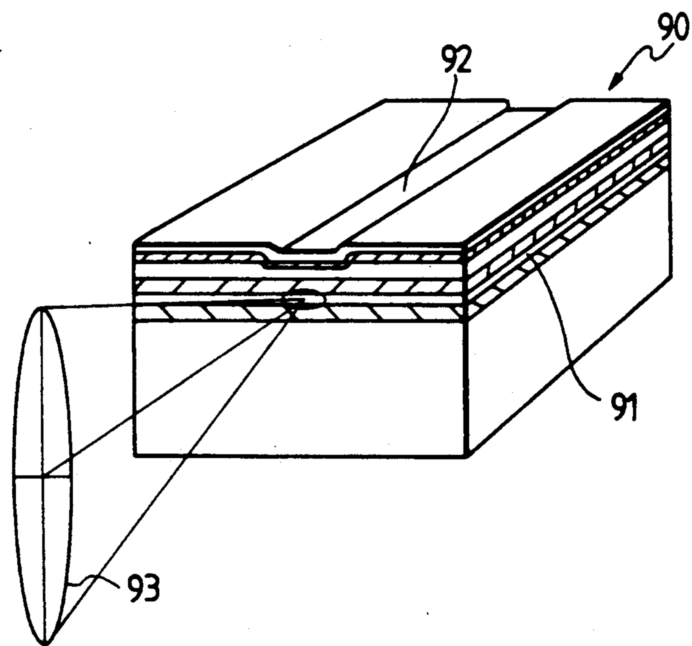
FIG. 8 is a perspective view showing a semiconductor laser and its output pattern.
Figure 9:
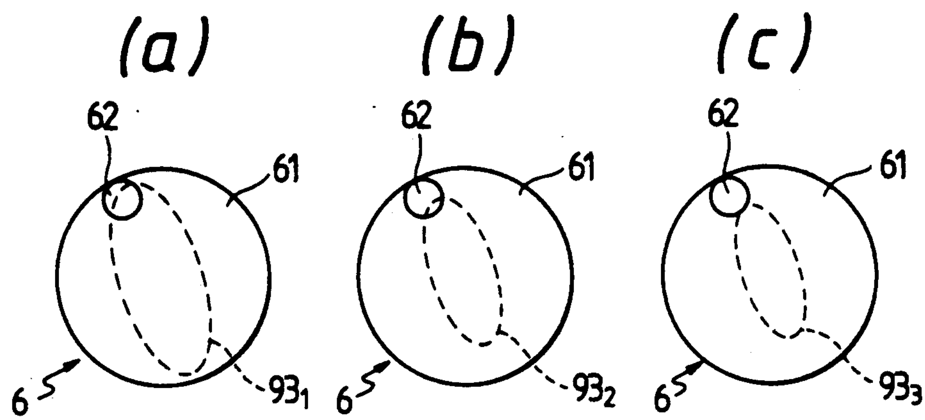
FIGS. 9(*a*), (*b*) and (*c*) are illustrations of the relationship between the input end of the optical fibre bundle and the output pattern of the light source at three different intensities.
Figure 10:
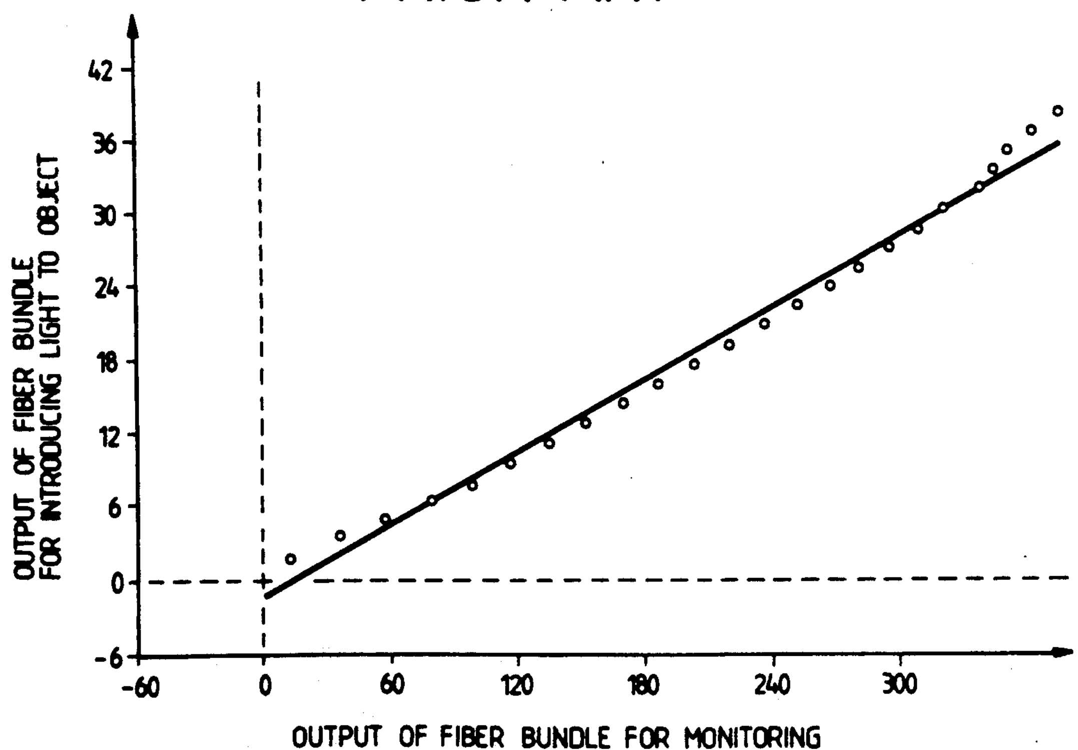
FIG. 10 is a graph showing the ratio of light output by the first and second branches in a conventional apparatus.

FIGS. 2(*a*) and 2(*b*) show a main portion of a second example which again replaces the optical fibre bundle shown in FIG. 7. In the second example the second branch fibre bundle 62 for monitoring is taken from one side of the incident face as it is in FIG. 7. This second embodiment is however different from the conventional example in FIG. 7 in that a mode scrambler 64 is interposed between the glass window 23 of the laser light source and the light incident end face of the optical fibre bundle 6. The mode scrambler 64 may be formed of a glass rod with its outside cylindrical face silvered, or may be formed as a thick clad optical fibre having a core diameter substantially the same as that of the fibre bundle 6. When the mode scrambler 64 is used, the laser output of an oval pattern emitted from the laser light source 2 is converted into uniform illumination having a circular pattern, so that again the light incident on the end faces of the fibres in the second branch fibre bundle 62 for monitoring corresponds to that in the first branch 61, so that the output power can be accurately monitored.

Figure 3:
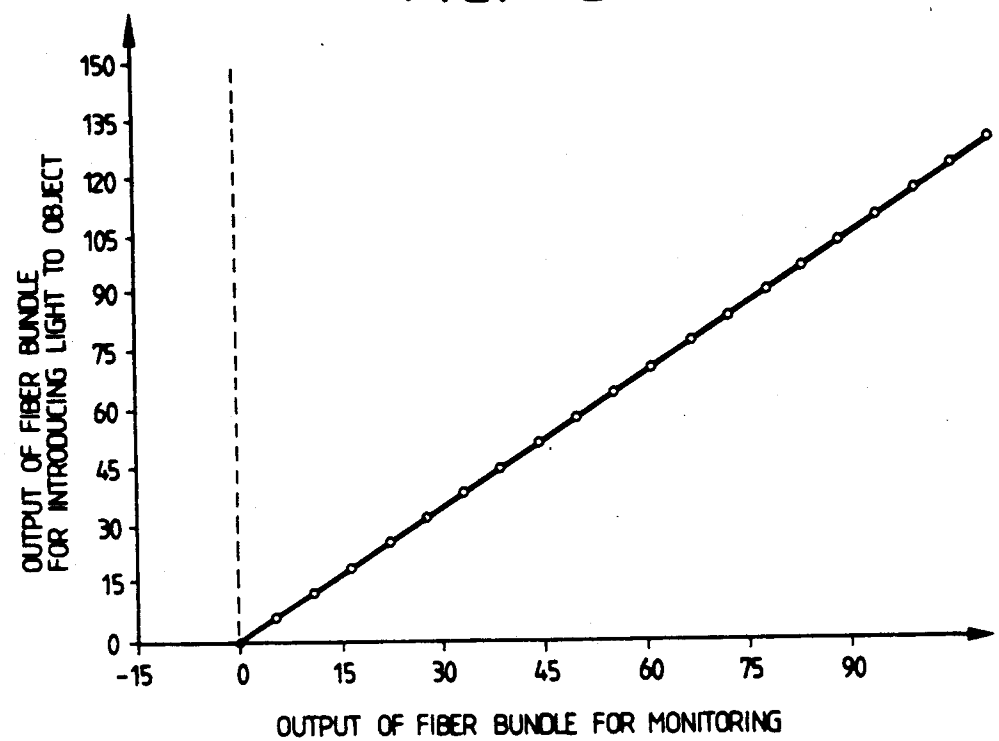
FIG. 3 is a graph showing the ratio of light output by the first and second branches according to the present invention.
Figure 5:
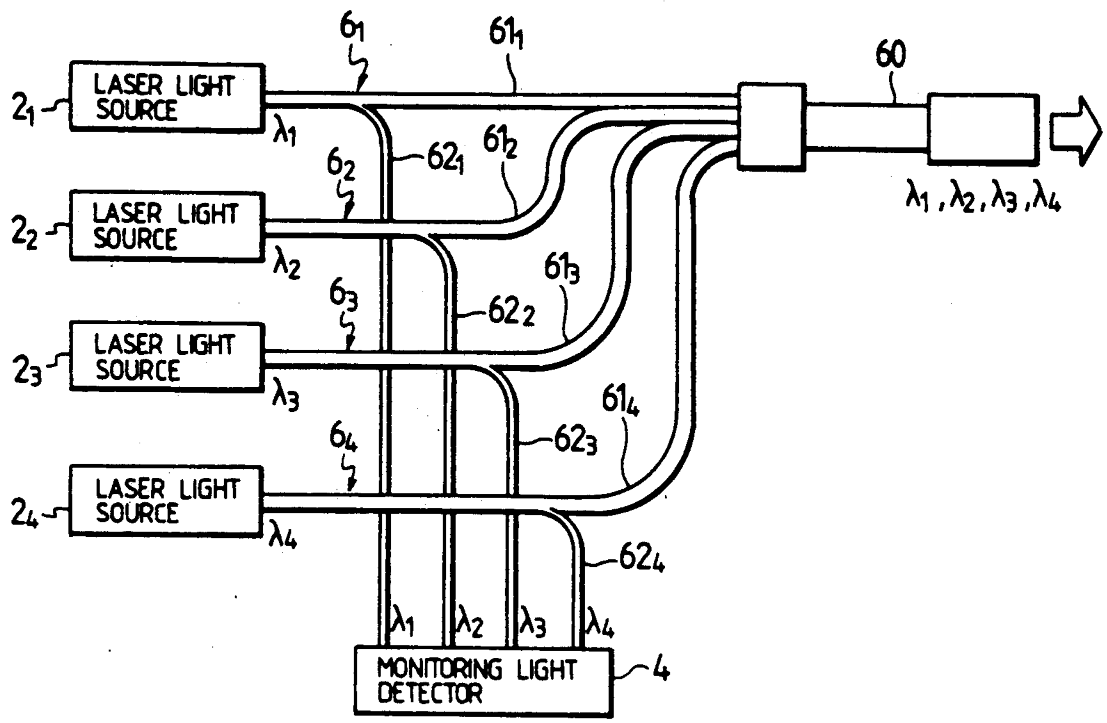
FIG. 5 is a block diagram of the light source and light monitor of an apparatus having a number of different lasers.
Figure 6:
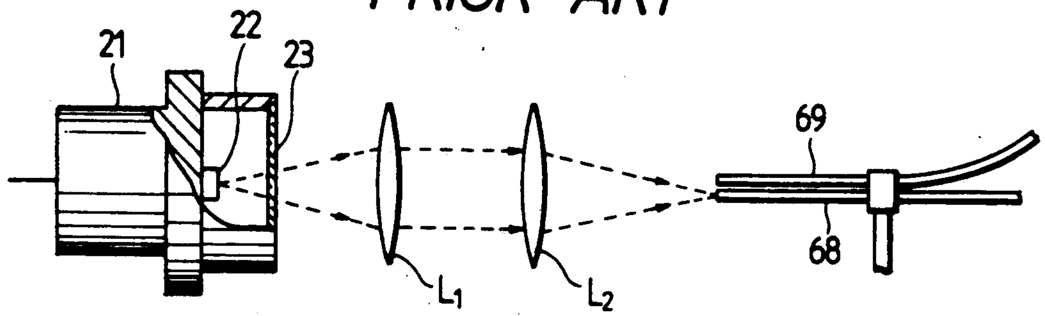
FIGS. 6 and 7 (*a*) and (*b*) are views each showing the arrangement of a light source and an optical fibre bundle in a conventional optical examination apparatus.

FIG. 3 shows the result of measurement by means of the first and second examples described above with relative scales. In the drawing, the axis of ordinate indicates the output of the first branch fibre bundle 61 for introducing light to organic tissues, while the axis of abscissa indicates the output of the second branch fibre bundle 62 for monitoring. As shown in the drawing, there is a substantially accurate linear relationship between the outputs with an error not larger than 1%. When the arrangements shown in FIGS. 1 and 2 are applied to the optical fibre bundle of the optical examination apparatus shown in FIG. 4 or 5, even if a semiconductor laser having large variations in its output is used for a light source, the transmitted and scattered light produced from an object to be examined can be compensated so accurately that an extremely accurate result of examination can be obtained.

As described above, by providing representative sampling means according to the present invention, in spite of variations in luminous pattern, the laser light can be made incident on the second monitoring branch fibre bundle with a predetermined and constant rate so that variations in luminous output can be accurately monitored. Accordingly, the optical examination can be correctly carried out even in the case where variations occur not only in a luminous output of the laser source (for example, a semiconductor laser) but also in a luminous pattern of the laser source.

What is claimed is:

1. An optical examination apparatus, for optically examining characteristics of oxygen in an object including the density and distribution of oxygen in the object, comprising:

a light source for emitting light having an intensity and a luminous pattern;

an optical fibre bundle having a first end for receiving said light emitted by said light source and a second end which is divided into a first branch fibre bundle for emitting an examination light onto the object so that said examination light is transmitted through and scattered by the object and a second branch fibre bundle for emitting a monitoring light, said monitoring light having an intensity and said first and second branch fibre bundles having a predetermined ratio of division where the first fibre bundle includes a substantially greater number of fibres than the second fibre bundle;

a transmitted and scattered light detection means for detecting light from said first fibre bundle and for providing a signal corresponding to said examination light transmitted through and scattered by the object;

a monitoring light detection means for detecting light from said second fibre bundle and for providing a signal corresponding to said monitoring light;

normalization means for normalizing said signal provided by said transmitted and scattered light detection means in accordance with said signal provided by said monitoring light detection means; and means for distributing irregularities in light intensity of said light emitted by said light source throughout the total area of the first end of said optical fibre bundle, and for emitting light at said second branch fibre bundle having an intensity corresponding to the predetermined ratio of the total light received at said first end of said optical fibre bundle.

2. The optical examination apparatus according to claim 1, wherein said means for distributing irregularities in light intensity comprises optical fibres forming said second branch fibre bundle and being uniformly distributed in the predetermined ratio relative to the fibres forming said first bundle throughout said first end of said optical fibre bundle.

3. The optical examination apparatus according to claim 1, wherein said means for distributing irregularities in light intensity comprises a glass rod interposed between said first end of said optical fibre bundle and said light source for uniformly distributing said irregular light intensity emitted by said light source onto said first end of said optical fibre bundle.

4. The optical examination apparatus according to claim 1, wherein said light source comprises a plurality of light sources for emitting light of different wavelengths and wherein said optical fibre bundle comprises a plurality of fibre bundles each associated with one of said plurality of light sources, respectively.

5. The optical examination apparatus according to claim 1, wherein said light source comprises at least one semiconductor laser.

6. The optical examination apparatus according to claim 1, wherein said light emitted by said light source is in the near infrared region of the electromagnetic wave spectrum.

* * * * *